United States Patent
Smith et al.

(10) Patent No.: US 10,363,086 B2
(45) Date of Patent: Jul. 30, 2019

(54) POWER MONITORING CIRCUITRY AND METHOD FOR REDUCING LEAKAGE CURRENT IN RF GENERATORS

(71) Applicant: Medtronic Advanced Energy LLC, Minneapolis, MN (US)

(72) Inventors: Jesse A. Smith, Portsmouth, NH (US); David Hubelbank, Manchester, NH (US); Jeffrey S. Reaume, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 691 days.

(21) Appl. No.: 14/927,969

(22) Filed: Oct. 30, 2015

(65) Prior Publication Data

US 2016/0120591 A1  May 5, 2016

Related U.S. Application Data

(60) Provisional application No. 62/164,930, filed on May 21, 2015, provisional application No. 62/073,705, filed on Oct. 31, 2014.

(51) Int. Cl.
*A61B 18/12* (2006.01)
*A61B 18/00* (2006.01)
*A61B 18/14* (2006.01)

(52) U.S. Cl.
CPC ...... *A61B 18/1233* (2013.01); *A61B 18/1206* (2013.01); *A61B 18/1402* (2013.01);
(Continued)

(58) Field of Classification Search
CPC . A61B 18/12; A61B 18/1206; A61B 18/1233; A61B 18/14; A61B 18/1402;
(Continued)

(56) References Cited

U.S. PATENT DOCUMENTS

| 39,358 A | 7/1863 | Smith |
| 41,921 A | 3/1864 | Holmes |

(Continued)

FOREIGN PATENT DOCUMENTS

| CN | 102641152 | 3/2014 |
| DE | 3420339 | 1/1985 |

(Continued)

OTHER PUBLICATIONS

PCT International Search Report dated Jan. 27, 2017, 4 pages.
(Continued)

*Primary Examiner* — Michael F Peffley
*Assistant Examiner* — Khadijeh A Vahdat
(74) *Attorney, Agent, or Firm* — Christopher & Weisberg, P.A.

(57) ABSTRACT

An electrosurgical unit having power monitoring circuitry for reducing leakage current in an electrosurgical unit. The electrosurgical unit includes a power source configured to produce direct current, an RF waveform generator configured to convert the direct current into an RF signal, a voltage sensor configured to measure DC input voltage to the RF waveform generator, a current sensor configured to measure output current feedback, and a processor. The processor is configured to estimate output voltage feedback based at least upon the measured DC input voltage and the measured output current feedback, and output a control signal to control the DC input voltage to the RF waveform generator, the control signal based at least upon the estimated output voltage and the output current feedback.

12 Claims, 6 Drawing Sheets

(52) U.S. Cl.
CPC ..... *A61B 18/148* (2013.01); *A61B 2018/0016* (2013.01); *A61B 2018/00178* (2013.01); *A61B 2018/00607* (2013.01); *A61B 2018/00642* (2013.01); *A61B 2018/00648* (2013.01); *A61B 2018/00666* (2013.01); *A61B 2018/00702* (2013.01); *A61B 2018/00767* (2013.01); *A61B 2018/00827* (2013.01); *A61B 2018/00875* (2013.01); *A61B 2018/00892* (2013.01); *A61B 2018/124* (2013.01); *A61B 2018/126* (2013.01); *A61B 2018/1253* (2013.01); *A61B 2018/1286* (2013.01)

(58) Field of Classification Search
CPC .......... A61B 18/148; A61B 2018/0016; A61B 2018/00178; A61B 2018/00607; A61B 2018/00642; A61B 2018/00648; A61B 2018/00666; A61B 2018/00702; A61B 2018/00767; A61B 2018/00827; A61B 2018/00875; A61B 2018/00892; A61B 2018/124; A61B 2018/1253; A61B 2018/126; A61B 2018/1286
USPC ..................................................... 606/33–41
See application file for complete search history.

(56) References Cited

U.S. PATENT DOCUMENTS

| | | | |
|---|---|---|---|
| 404,004 A | 5/1889 | Hovey | |
| 411,004 A | 9/1889 | Billings | |
| 4,473,075 A | 9/1984 | Rexroth | |
| 4,569,345 A | 2/1986 | Manes | |
| 4,903,696 A | 2/1990 | Stasx et al. | |
| 5,282,799 A | 2/1994 | Rydell | |
| 5,300,068 A | 4/1994 | Rosar et al. | |
| 5,334,193 A | 8/1994 | Nardella | |
| 5,352,868 A | 10/1994 | Denen et al. | |
| 5,422,567 A | 6/1995 | Matsunaga | |
| 5,438,302 A | 8/1995 | Goble | |
| 5,558,671 A | 9/1996 | Yates | |
| 5,573,424 A | 11/1996 | Poppe | |
| 5,582,610 A | 12/1996 | Grossi et al. | |
| 5,599,349 A | 2/1997 | D'Amelio | |
| 5,647,869 A | 7/1997 | Goble et al. | |
| 5,669,906 A | 9/1997 | Grossi et al. | |
| 5,707,369 A | 1/1998 | Vaitekunas et al. | |
| 5,720,744 A | 2/1998 | Eggleston et al. | |
| 5,766,153 A | 6/1998 | Eggers et al. | |
| 5,772,659 A | 6/1998 | Becker et al. | |
| 5,792,138 A | 8/1998 | Shipp | |
| 5,810,804 A | 9/1998 | Gough et al. | |
| 5,860,975 A | 1/1999 | Goble et al. | |
| 5,888,198 A | 3/1999 | Eggers et al. | |
| 5,944,715 A | 8/1999 | Goble et al. | |
| 6,004,319 A | 12/1999 | Goble et al. | |
| 6,013,076 A | 1/2000 | Goble et al. | |
| 6,015,406 A | 1/2000 | Goble et al. | |
| 6,027,501 A | 2/2000 | Goble et al. | |
| 6,039,734 A | 3/2000 | Goble | |
| 6,056,746 A | 5/2000 | Goble et al. | |
| 6,059,780 A | 5/2000 | Gough et al. | |
| 6,074,386 A | 6/2000 | Goble et al. | |
| 6,090,106 A | 7/2000 | Goble et al. | |
| 6,093,186 A | 7/2000 | Goble | |
| 6,100,920 A | 8/2000 | Miller et al. | |
| 6,142,992 A | 11/2000 | Cheng et al. | |
| 6,151,381 A | 11/2000 | Grodzins et al. | |
| 6,174,308 B1 | 1/2001 | Goble et al. | |
| 6,197,025 B1 | 3/2001 | Grossi et al. | |
| 6,203,541 B1 | 3/2001 | Keppel | |
| 6,210,405 B1 | 4/2001 | Goble et al. | |
| 6,228,081 B1 | 5/2001 | Goble | |
| 6,234,178 B1 | 5/2001 | Goble et al. | |
| 6,238,388 B1 | 5/2001 | Ellman et al. | |
| 6,251,106 B1 | 6/2001 | Becker et al. | |
| 6,258,085 B1 | 7/2001 | Eggleston | |
| 6,261,286 B1 | 7/2001 | Goble et al. | |
| 6,277,114 B1 | 8/2001 | Bullivant et al. | |
| 6,293,941 B1 | 9/2001 | Strul et al. | |
| 6,293,942 B1 | 9/2001 | Goble et al. | |
| 6,298,255 B1 | 10/2001 | Cordero et al. | |
| 6,306,134 B1 | 10/2001 | Goble et al. | |
| 6,322,494 B1 | 11/2001 | Bullivant et al. | |
| 6,325,799 B1 | 12/2001 | Goble | |
| 6,336,926 B1 | 1/2002 | Goble | |
| 6,364,877 B1 | 4/2002 | Goble et al. | |
| 6,370,408 B1 | 4/2002 | Merchant et al. | |
| 6,385,059 B1 | 5/2002 | Telefus et al. | |
| 6,398,781 B1 | 6/2002 | Goble et al. | |
| 6,402,742 B1 | 6/2002 | Blewett et al. | |
| 6,416,509 B1 | 7/2002 | Gobel et al. | |
| 6,458,121 B1 | 10/2002 | Rosenstock et al. | |
| 6,482,202 B1 | 11/2002 | Gobel et al. | |
| 6,488,678 B2 | 12/2002 | Sherman | |
| 6,491,690 B1 | 12/2002 | Gobel et al. | |
| 6,508,815 B1 | 1/2003 | Strul et al. | |
| 6,544,260 B1 | 4/2003 | Markel et al. | |
| 6,547,786 B1 | 4/2003 | Goble | |
| 6,557,559 B1 | 5/2003 | Eggers et al. | |
| 6,558,379 B1 | 5/2003 | Batchelor et al. | |
| 6,565,559 B2 | 5/2003 | Eggleston | |
| 6,565,560 B1 | 5/2003 | Gobel et al. | |
| 6,565,561 B1 | 5/2003 | Gobel et al. | |
| 6,582,427 B1 | 6/2003 | Gobel et al. | |
| 6,611,141 B1 | 8/2003 | Schulz et al. | |
| 6,723,091 B2 | 4/2004 | Gobel et al. | |
| 6,758,846 B2 | 7/2004 | Gobel et al. | |
| 6,761,716 B2 | 7/2004 | Kadhiresan et al. | |
| 6,784,405 B2 | 8/2004 | Flugstad et al. | |
| 6,808,525 B2 | 10/2004 | Latterell et al. | |
| 6,832,998 B2 | 12/2004 | Goble | |
| 6,843,789 B2 | 1/2005 | Goble | |
| 6,875,210 B2 | 4/2005 | Refior et al. | |
| 6,893,435 B2 | 5/2005 | Goble | |
| 6,923,803 B2 | 8/2005 | Goble | |
| 6,929,641 B2 | 8/2005 | Gobel et al. | |
| 6,936,047 B2 | 8/2005 | Nasab et al. | |
| 6,942,660 B2 | 9/2005 | Pantera et al. | |
| 6,948,503 B2 | 9/2005 | Refior et al. | |
| 6,953,461 B2 | 10/2005 | McClurken et al. | |
| 6,966,907 B2 | 11/2005 | Goble | |
| 6,984,231 B2 | 1/2006 | Gobel et al. | |
| 7,001,380 B2 | 2/2006 | Goble | |
| 7,041,096 B2 | 5/2006 | Malis et al. | |
| 7,060,063 B2 | 6/2006 | Marion et al. | |
| 7,137,980 B2 | 11/2006 | Buysse et al. | |
| 7,146,210 B2 | 12/2006 | Palti | |
| 7,147,637 B2 | 12/2006 | Goble | |
| 7,153,300 B2 | 12/2006 | Goble | |
| 7,169,144 B2 | 1/2007 | Hoey et al. | |
| 7,195,627 B2 | 3/2007 | Amoah et al. | |
| 7,201,750 B1 | 4/2007 | Eggers et al. | |
| 7,211,081 B2 | 5/2007 | Goble | |
| 7,211,084 B2 | 5/2007 | Gobel et al. | |
| 7,214,224 B2 | 5/2007 | Goble | |
| 7,247,155 B2 | 7/2007 | Hoey et al. | |
| 7,250,048 B2 | 7/2007 | Francischelli et al. | |
| 7,255,696 B2 | 8/2007 | Gobel et al. | |
| 7,278,994 B2 | 10/2007 | Goble | |
| 7,282,048 B2 | 10/2007 | Gobel et al. | |
| 7,300,436 B2 | 11/2007 | Penny et al. | |
| 7,322,975 B2 | 1/2008 | Gobel et al. | |
| 7,335,199 B2 | 2/2008 | Gobel et al. | |
| 7,344,532 B2 | 3/2008 | Gobel et al. | |
| 7,367,972 B2 | 5/2008 | Francischelli et al. | |
| D574,323 S | 8/2008 | Waaler | |
| 7,422,582 B2 | 9/2008 | Malackowski et al. | |
| 7,429,261 B2 | 9/2008 | Kunis et al. | |
| 7,442,191 B2 | 10/2008 | Hovda et al. | |
| 7,491,199 B2 | 2/2009 | Goble | |
| 7,651,513 B2 | 1/2010 | Teoh et al. | |
| 7,674,263 B2 | 3/2010 | Ryan | |
| 7,699,846 B2 | 4/2010 | Ryan | |

(56) References Cited

U.S. PATENT DOCUMENTS

| | | |
|---|---|---|
| 7,708,733 B2 | 5/2010 | Sanders et al. |
| 7,717,910 B2 | 5/2010 | Goble |
| 7,799,020 B2 | 9/2010 | Shores et al. |
| 7,850,684 B2 | 12/2010 | Marshall et al. |
| 7,854,736 B2 | 12/2010 | Ryan |
| 7,855,727 B2 | 12/2010 | Adler et al. |
| 7,887,534 B2 | 2/2011 | Hamel et al. |
| 7,887,536 B2 | 2/2011 | Johnson et al. |
| 7,896,877 B2 | 3/2011 | Hall et al. |
| 7,927,328 B2 | 4/2011 | Orszulak et al. |
| 7,956,620 B2 | 6/2011 | Gilbert |
| 7,976,544 B2 | 7/2011 | McClurken et al. |
| 7,993,332 B2 | 8/2011 | Gobel et al. |
| 8,002,769 B2 | 8/2011 | Gobel et al. |
| 8,034,049 B2 | 10/2011 | Odom et al. |
| 8,045,943 B2 | 10/2011 | Kaczman et al. |
| 8,082,043 B2 | 12/2011 | Sharkey et al. |
| 8,175,590 B2 | 5/2012 | Hamel et al. |
| 8,192,424 B2 | 6/2012 | Woloszko |
| 8,226,680 B2 | 7/2012 | Wallace |
| 8,241,284 B2 | 8/2012 | Dycus et al. |
| 8,246,616 B2 | 8/2012 | Amoah et al. |
| 8,251,989 B1 | 8/2012 | Newton et al. |
| 8,257,350 B2 | 9/2012 | Marion |
| 8,273,084 B2 | 9/2012 | Kunis et al. |
| 8,273,085 B2 | 9/2012 | Park et al. |
| 8,333,760 B2 | 12/2012 | Roggan et al. |
| 8,355,799 B2 | 1/2013 | Marion et al. |
| 8,444,638 B2 | 5/2013 | Woloszko et al. |
| 8,452,422 B2 | 5/2013 | Desinger et al. |
| 8,512,340 B2 | 8/2013 | Easley et al. |
| 8,551,088 B2 | 10/2013 | Falkenstein et al. |
| 8,562,598 B2 | 10/2013 | Falkenstein et al. |
| 8,568,405 B2 | 10/2013 | Cox et al. |
| 8,568,411 B2 | 10/2013 | Falkenstein et al. |
| 8,574,187 B2 | 11/2013 | Marion |
| 8,579,894 B2 | 11/2013 | Falkenstein et al. |
| 8,597,287 B2 | 12/2013 | Benamou et al. |
| 8,617,151 B2 | 12/2013 | Denis et al. |
| 8,657,817 B2 | 2/2014 | Fischer et al. |
| 8,672,934 B2 | 3/2014 | Benamou et al. |
| 8,685,018 B2 | 4/2014 | Cox et al. |
| 8,696,659 B2 | 4/2014 | Marion |
| 8,747,399 B2 | 6/2014 | Woloszko et al. |
| 8,747,401 B2 | 6/2014 | Gonzalez et al. |
| 8,784,415 B2 | 7/2014 | Malackowski et al. |
| 8,790,335 B2 | 7/2014 | Gilbert |
| 8,801,705 B2 | 8/2014 | Sanders et al. |
| 8,870,866 B2 | 10/2014 | Woloszko |
| 8,900,226 B2 | 12/2014 | Silig et al. |
| 8,915,910 B2 | 12/2014 | Falkenstein et al. |
| 8,920,412 B2 | 12/2014 | Fritz et al. |
| 8,932,291 B2 | 1/2015 | Orszulak |
| 9,008,757 B2 | 4/2015 | Wu |
| 9,033,973 B2 | 5/2015 | Krapohl et al. |
| 9,066,735 B2 | 6/2015 | Williams |
| 9,095,358 B2 | 8/2015 | Woloszko et al. |
| 9,099,863 B2 | 8/2015 | Smith et al. |
| 9,138,282 B2 | 9/2015 | Marion |
| 9,270,202 B2 | 2/2016 | Johnson et al. |
| 9,498,276 B2 | 11/2016 | Gilbert |
| 2001/0014003 A1 | 8/2001 | Dible |
| 2003/0050633 A1 | 3/2003 | Ellman et al. |
| 2003/0083652 A1 | 5/2003 | Markel |
| 2003/0181964 A1 | 9/2003 | Sharkey et al. |
| 2004/0199175 A1 | 10/2004 | Jaeger et al. |
| 2005/0113820 A1 | 5/2005 | Goble et al. |
| 2005/0177184 A1 | 8/2005 | Easley |
| 2006/0004396 A1 | 1/2006 | Easley et al. |
| 2006/0106375 A1 | 5/2006 | Werneth et al. |
| 2006/0142753 A1 | 6/2006 | Francischelli et al. |
| 2006/0149225 A1 | 7/2006 | McClurken |
| 2007/0073334 A1 | 3/2007 | Rarnzipoor |
| 2007/0083193 A1 | 4/2007 | Werneth et al. |
| 2007/0083195 A1 | 4/2007 | Werneth et al. |
| 2007/0085496 A1 | 4/2007 | Philipp et al. |
| 2007/0104610 A1 | 5/2007 | Houston et al. |
| 2007/0129716 A1 | 6/2007 | Daw et al. |
| 2007/0167941 A1 | 7/2007 | Hamel et al. |
| 2007/0173803 A1 | 7/2007 | Wham et al. |
| 2007/0173806 A1 | 7/2007 | Orszulak et al. |
| 2007/0173813 A1 | 7/2007 | Odom |
| 2007/0225550 A1 | 9/2007 | Gattani et al. |
| 2008/0039831 A1 | 2/2008 | Odom et al. |
| 2008/0082095 A1 | 4/2008 | Shores et al. |
| 2008/0082096 A1 | 4/2008 | Shores et al. |
| 2008/0082100 A1 | 4/2008 | Orton et al. |
| 2008/0108940 A1 | 5/2008 | Sharkey et al. |
| 2008/0281311 A1 | 11/2008 | Dunning et al. |
| 2008/0281312 A1 | 11/2008 | Werneth et al. |
| 2008/0281322 A1 | 11/2008 | Sherman et al. |
| 2009/0182325 A1 | 7/2009 | Werneth et al. |
| 2009/0234350 A1 | 9/2009 | Behnke et al. |
| 2009/0275940 A1 | 11/2009 | Malackowski et al. |
| 2009/0292283 A1 | 11/2009 | Odom |
| 2009/0306648 A1 | 12/2009 | Podhajsky et al. |
| 2010/0016857 A1 | 1/2010 | McKenna et al. |
| 2010/0042093 A9 | 2/2010 | Wham et al. |
| 2010/0079215 A1 | 4/2010 | Brannan et al. |
| 2010/0082022 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0179534 A1 | 7/2010 | Podhajsky et al. |
| 2010/0179535 A1 | 7/2010 | Podhajsky et al. |
| 2010/0179538 A1 | 7/2010 | Podhajsky |
| 2010/0241115 A1 | 9/2010 | Benamou et al. |
| 2010/0241116 A1 | 9/2010 | Benamou et al. |
| 2010/0324550 A1 | 12/2010 | Morgan et al. |
| 2010/0331666 A1 | 12/2010 | Wallace |
| 2011/0037484 A1 | 2/2011 | Gilbert |
| 2011/0071516 A1 | 3/2011 | Gregg |
| 2011/0071521 A1 | 3/2011 | Gilberg |
| 2011/0077631 A1 | 3/2011 | Keller |
| 2011/0144635 A1 | 6/2011 | Harper et al. |
| 2011/0178515 A1 | 7/2011 | Bloom et al. |
| 2011/0178516 A1 | 7/2011 | Orszulak et al. |
| 2011/0204903 A1 | 8/2011 | Gilbert |
| 2011/0270237 A1 | 11/2011 | Werneth et al. |
| 2012/0095457 A1 | 4/2012 | Morgan et al. |
| 2012/0136346 A1 | 5/2012 | Condie et al. |
| 2012/0136347 A1 | 5/2012 | Brustad et al. |
| 2012/0136348 A1 | 5/2012 | Condie et al. |
| 2012/0157985 A1 | 6/2012 | Ballou et al. |
| 2012/0197243 A1 | 8/2012 | Sherman et al. |
| 2012/0215216 A1 | 8/2012 | Friedrichs et al. |
| 2012/0265196 A1 | 10/2012 | Turner et al. |
| 2013/0035679 A1 | 2/2013 | Orszulak |
| 2013/0053840 A1 | 2/2013 | Krapohl et al. |
| 2013/0253502 A1 | 9/2013 | Aronow et al. |
| 2013/0274729 A1 | 10/2013 | Orszulak |
| 2014/0018795 A1 | 1/2014 | Shilev et al. |
| 2014/0025061 A1 | 1/2014 | Benamou |
| 2014/0039517 A1 | 2/2014 | Bowling et al. |
| 2014/0052123 A1 | 2/2014 | Benamou et al. |
| 2014/0062308 A1 | 3/2014 | Nakajima |
| 2014/0200621 A1 | 7/2014 | Malackowski et al. |
| 2014/0232316 A1 | 8/2014 | Philipp |
| 2014/0276750 A1 | 9/2014 | Gilbert |
| 2014/0276754 A1 | 9/2014 | Gilbert et al. |
| 2014/0276768 A1 | 9/2014 | Juergens et al. |
| 2014/0324039 A1 | 10/2014 | Malackowski et al. |
| 2015/0088118 A1 | 3/2015 | Gilbert et al. |
| 2015/0223865 A1 | 8/2015 | Krapohl et al. |
| 2015/0230861 A1 | 8/2015 | Woloszko et al. |

FOREIGN PATENT DOCUMENTS

| | | |
|---|---|---|
| EP | 336742 | 10/1989 |
| EP | 608609 | 3/1994 |
| EP | 325456 | 12/1995 |

(56) References Cited

FOREIGN PATENT DOCUMENTS

| | | |
|---|---|---|
| EP | 880220 | 4/1998 |
| EP | 1776929 | 10/2006 |
| EP | 2393208 A2 | 12/2011 |
| EP | 2474165 | 7/2012 |
| JP | 2000271145 A | 10/2000 |
| JP | 2006506172 A | 2/2006 |
| WO | 9847436 A1 | 10/1998 |
| WO | 0211634 | 2/2002 |
| WO | 0245589 | 6/2002 |
| WO | 03090634 | 11/2003 |
| WO | 2008043999 A2 | 4/2008 |

OTHER PUBLICATIONS

Valleylab™, Service Manual, Force FX™-8C Electrosurgical Generator with Instant Response™ Technology, Sep. 2000, pp. 1-218.
Force 4 Service Manual, May 1, 1985, Valleylab Part No. A945 100 055A, pp. 1-144.

POWER MONITORING CIRCUITRY AND METHOD FOR REDUCING LEAKAGE CURRENT IN RF GENERATORS

CROSS-REFERENCE TO RELATED APPLICATION

This application is related to and claims priority to U.S. Provisional Patent Application Ser. No. 62/073,705, filed Oct. 31, 2014, entitled COMBINATION PEAK PLASMA AND TRANSCOLLATION TIP, and claims priority to U.S. Provisional Patent Application Ser. No. 62/164,930, filed May 21, 2015, entitled ELECTROSURGICAL GENERATOR the entirety of which is incorporated herein by reference.

STATEMENT REGARDING FEDERALLY SPONSORED RESEARCH OR DEVELOPMENT n/a

TECHNICAL FIELD

The present disclosure relates to electrosurgical units having radio frequency generators and more specifically to a method and system for managing power output and reducing leakage current from the electrosurgical unit.

BACKGROUND

In radiofrequency ("RF") therapeutic systems, all monopolar therapeutic energy produced by a RF generator should theoretically return to the generator via a patient return electrode. The therapeutic path typically flows from the RF generator to an active accessory, to a target, i.e., a patient, to a return electrode and back to the RF generator. However, due to the capacitance of transformers in isolation barriers which serve to isolate the supply of RF energy between the RF generator and the delivery device, sometimes stray leakage in the form of RF energy flows from the RF generator to ground instead of returning to the RF generator as part of the therapeutic path. RF leakage is a cause of concern to users because of the dangerous amount of current that can enter the patient, the surgeon or other medical personal that are in contact with the patient.

RF generator designers face the challenge of ensuring that the connection between the patient and the equipment in the RF therapeutic system minimizes leakage current under both normal system operation and under fault conditions. Designers are further faced with the challenge of meeting the isolation and leakage current requirements of Standard IEC60601, which defines the safety and electromagnetic compliance ("EMC") for medical systems.

Another challenge facing RF generator designers is the design of generators that comply with Standard IEC60601, particularly the standard that requires that the system maintains safe operation during any single fault condition and does not exceed the power output limits set forth by the IEC 60601 standard. While software exists that controls the output power based on feedback, other effective non-software implementations are required since a software failure alone cannot allow dangerous conditions to exist.

Typical RF generators have outputs that are isolated from ground in order to prevent RF leakage. However, isolated output circuits are, by themselves, not enough to completely eliminate RF leakage. Some RF generators have been designed with the capability of detecting open circuits and being able to lower their peak output voltage accordingly. This leads to several performance problems. Lowering peak output voltage in order to minimize leakage current may degrade the performance of the RF generator since the peak output voltage initiates the sparking needed for proper coagulation effect. Further, the amount of time needed by the generator to sense the open circuit condition may lead to momentary voltage spikes, which could cause RF leakage to occur.

Other types of predicate generators introduce throttling schemes when unacceptable leakage levels are detected. These throttling schemes have proven to be inadequate because they add undesired complexity to the control system.

FIG. 1 illustrates a circuit diagram of a typical feedback estimation system for use in an RF therapeutic system. Circuit 10 includes a direct current ("DC") power supply 11 that generates DC voltage which is passed into a voltage buck regulator by PWM control of a transistor 12. The PWM output waveform from transistor 12 is filtered through a filter 14 to create a reduced DC voltage that passes through an H-bridge RF wave generator 16 to be transformed into RF energy in the form of an RF waveform which is applied to an electrosurgical instrument (not shown), which is used to treat the target patient 18.

Continuing with the prior art circuitry illustrated in FIG. 1, the RF output circuit may include a high-turns transformer 22 across an isolation barrier 17, which serves to isolate a supply of RF energy from the electrosurgical instrument. A voltage sensor 28, which includes a voltage divider 20 and a high-turns transformer with couplings 24, measures RMS output voltage feedback at location (1) in circuit 10. Current sensor 30 also includes a transformer with couplings 26 and is configured to measure RMS output current feedback at location (2) in circuit 10. Thus, circuit 10 includes three inductive couplings, 22, 24 and 26, across isolation barrier 17. Based on the AC RMS output voltage feedback and the RMS output current feedback, a microprocessor 32 calculates an estimated output voltage and power and adjusts a control output Pulse Width Modulation ("PWM") signal output at location (4) to control the voltage input to H-bridge RF wave generator 16 and maintain its output at desired levels. However, the large number of inductance couplings in isolation barrier 17 result in excess capacitance and ultimately unduly high levels of leakage current. Therefore, a different RF feedback estimation circuit is desired.

SUMMARY

The present disclosure advantageously provides an electrosurgical unit having circuitry for reducing leakage current. In one embodiment, the electrosurgical unit includes a power source configured to produce direct current, an RF waveform generator configured to convert the direct current into an RF signal, a voltage sensor configured to measure DC input voltage to the RF waveform generator and a current sensor configured to measure output current feedback. The electrosurgical unit also includes a processor configured to estimate output voltage feedback based at least upon the measured DC input voltage and the measured output current feedback, and output a control signal to control the DC input voltage to the RF waveform generator, the control signal based at least upon the estimated output voltage and the output current feedback.

In another embodiment, a method for controlling power of an RF system is provided. The method includes measuring DC input voltage to an RF waveform generator, measuring output current feedback, estimating output voltage feedback based at least upon the measured DC input voltage and the measured output current feedback, and outputting a control signal to control the DC input voltage to the RF waveform generator, the control signal based at least upon the estimated output voltage and the output current feedback.

In another embodiment, the electrosurgical unit includes a DC power supply configured to supply DC supply current and DC voltage, a programmable logic device configured to receive a power limit setting and output a PWM signal, the PWM signal corresponding to the power limit setting, a buffer configured to convert the PWM signal to a threshold voltage, and a comparator. The comparator is configured to compare the product of the direct supply current and the DC voltage to the threshold voltage, and output an enable signal to the programmable logic device, the enable signal enabling the programmable logic device to output a PWM signal to allow the electrosurgical unit to control output of RF energy below the power limit setting.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

The embodiments described herein relate to circuits that can be employed in an electrosurgical unit such that the RF energy produced by an RF generator can be controlled so as not to exceed excessive power levels prohibited by safety standards. Further, the exemplary circuits described herein indirectly monitor the output voltage and output current of the RF waveform generators for excessively high power and/or current conditions, thus achieving a secondary, redundant mitigation for over-power conditions as prescribed by standards such as Standard IE 60601-2-2.

Figure 2:
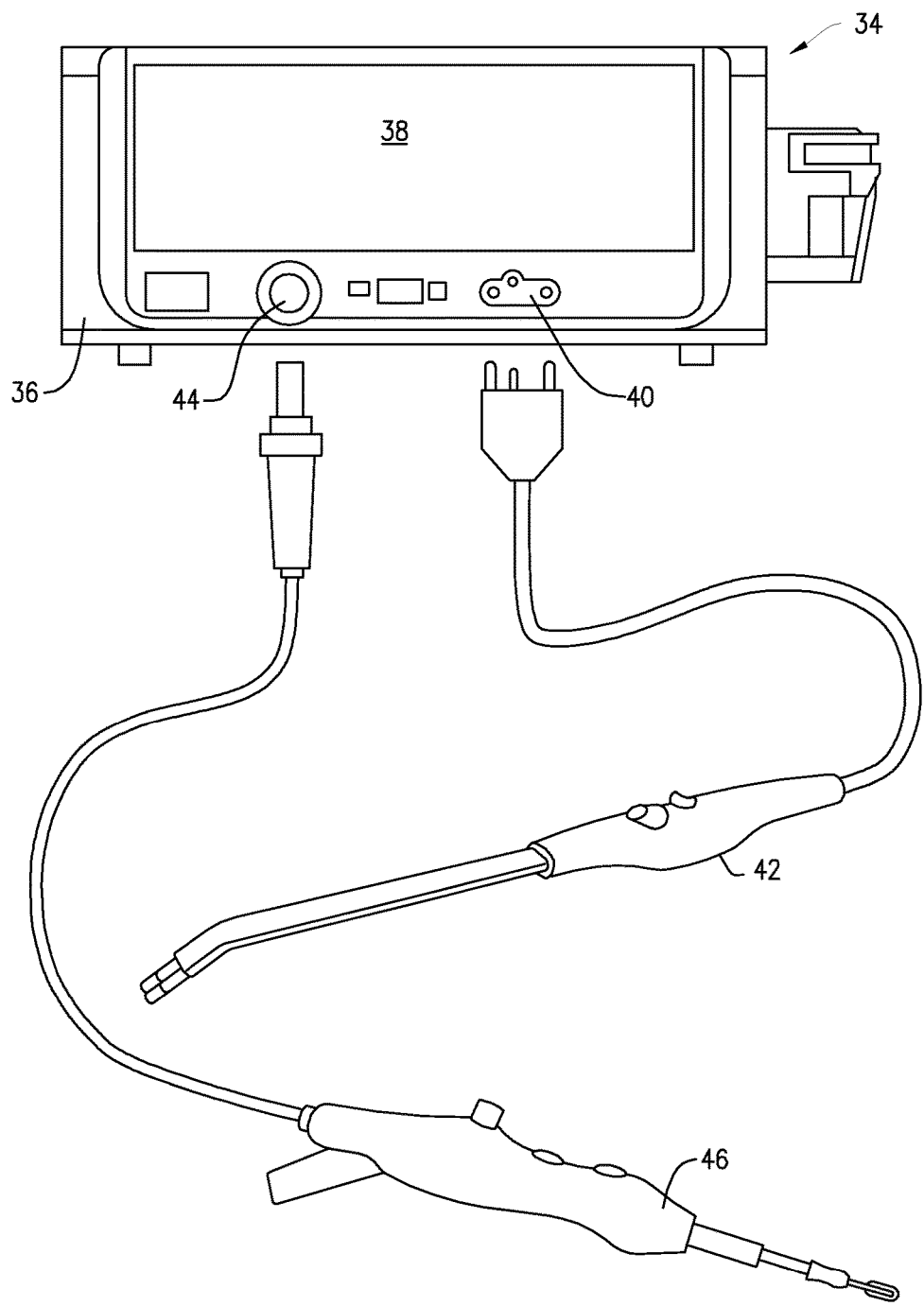
FIG. 2 is a front perspective view of an electrosurgical hand piece and electrosurgical unit constructed in accordance with the principles of the present disclosure.

Referring now to the drawings in which like reference designators refer to like elements, there is shown in FIG. 2 an exemplary electrosurgical unit ("ESU") constructed in accordance with the principles of the present application and designated generally as "34." ESU 34 may include a RF generator 36 configured to house the components of ESU 34 and may further include a touch actuated display 38 to configure energy output for one or more electrosurgical hand pieces that physically couple to the RF generator 36 (while maintaining electrical isolation between RF and the housing), display treatment progress and measurements, for example, impedance, and initiate and/or terminate the supply of radiofrequency energy and fluid rate of one or more electrosurgical hand pieces electrically coupled to ESU 34. In an exemplary configuration, ESU 34 includes a first receptacle 40, which may be a 3-pin connector configured to receive and electrical couple with a first electrosurgical hand piece 42 configured to deliver bipolar radiofrequency energy to tissue. ESU 34 may further include a second receptacle 44, for example, a 7-pin receptacle, configured to receive and electrically couple with a second electrosurgical hand piece 46 configured to deliver at least one of monopolar radiofrequency energy or a combination of bipolar radiofrequency energy and monopolar radiofrequency energy.

Figure 3:
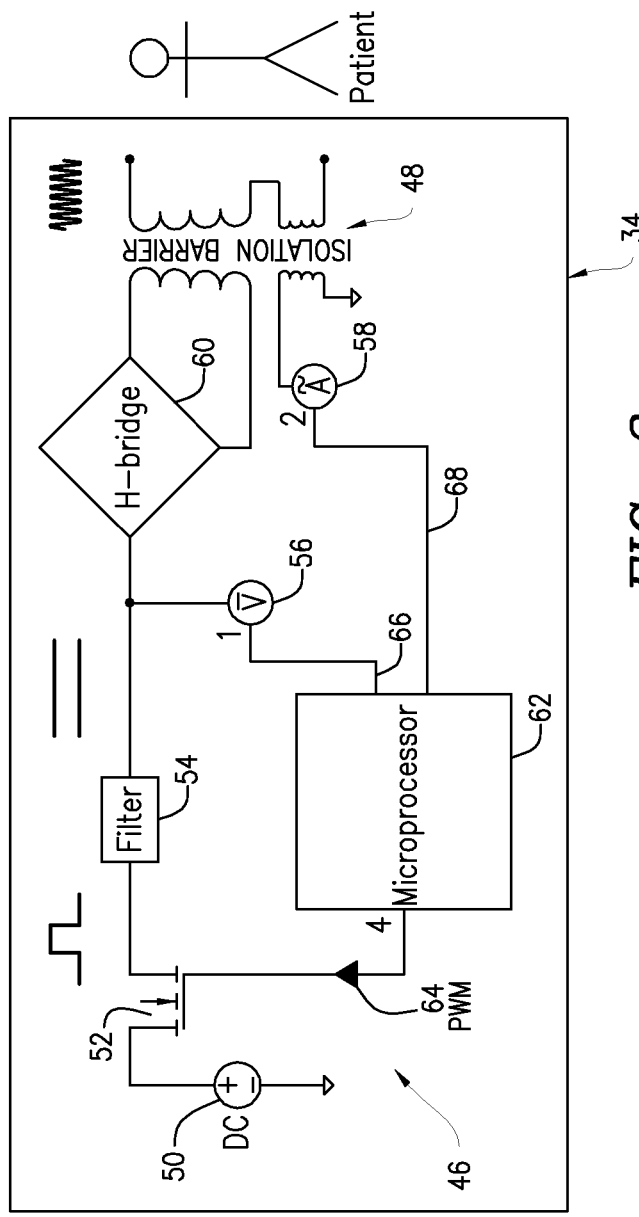
FIG. 3 illustrates feedback estimation circuitry for reducing leakage current according to an embodiment of the present disclosure.

FIG. 3 illustrates a circuit 46 within ESU 34 for providing indirect feedback estimation and for limiting leakage current in ESU 34 by reducing the number of circuit components, reducing the use of expensive RMS converters and transformers and reducing the number of inductance couplings across isolation barrier 48, which reduces capacitance and leakage current. Isolation barrier 48 includes one or more transformers that are configured to isolate a supply of RF energy between the RF generator 36 and one or more electrosurgical delivery devices (not shown). The design of circuit 46 results in reduced capacitance across isolation barrier 48 and therefore reduced patient leakage current. Circuit 46 is an indirect feedback estimation circuit that uses the DC voltage input measured by voltage sensor 56 rather than the sensed RMS feedback voltage across the output to control power output of RF generator 36. Circuit 46 includes a DC power source 50 configured to produce DC current, which is passed into a voltage buck regulator by PWM control of a transistor 52. Circuit 46 includes filter 54, which filters the PWM waveform into a reduced DC voltage, and voltage sensor 56 located at location (1) in circuit 46. Voltage sensor 56 measures the DC input voltage of the signal to an RF waveform generator 60. RF waveform generator 60 may include bridge circuitry configured to generate an RF signal from the DC input voltage adjusted by a microprocessor 62.

Figure 1:
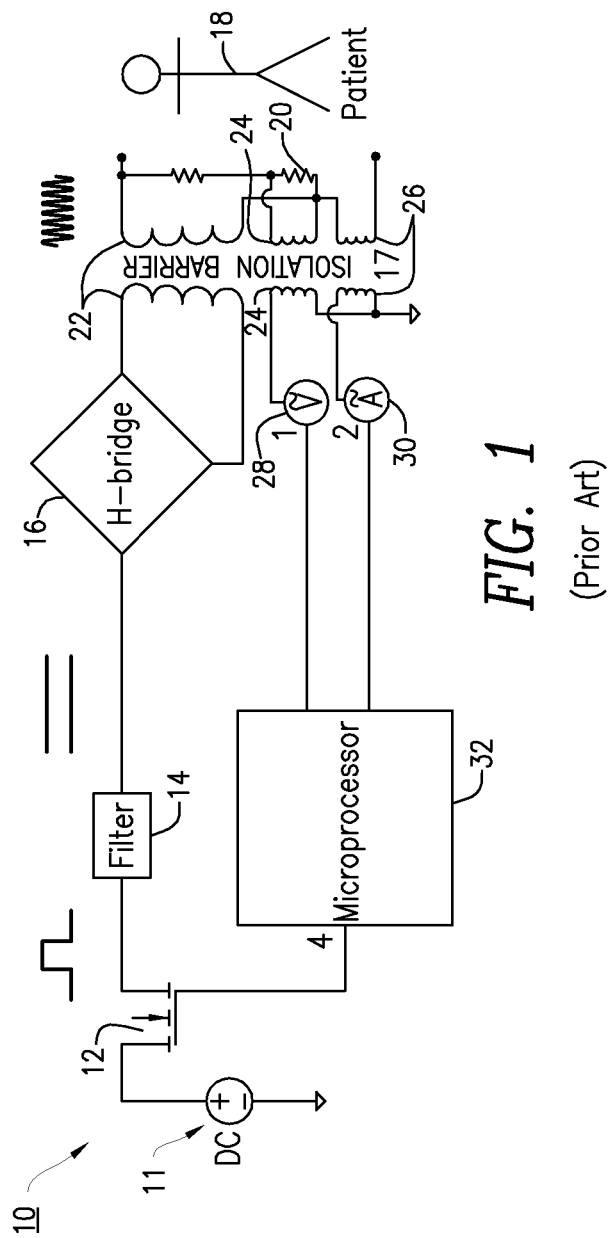
FIG. 1 illustrates a feedback estimation circuit of the prior art.

The DC input voltage feedback is one of two independent explanatory variables that can be used to estimate the dependent variable RMS output voltage. The other independent explanatory variable used is the AC RMS output current measured by current sensor 58 at location (2) in circuit 46. Advantageously, circuit 46 does not require the measurement of the output voltage feedback shown in the prior art circuit of FIG. 1. Thus, components needed to measure the output voltage feedback, i.e., transformers across the isolation barrier 48, are not needed. The reduction of inductance couplings across isolation barrier 48 (in this case, reduced from three couplings as shown in FIG. 1 to two shown in FIG. 3) reduces the overall capacitance at isolation barrier 48, thus reducing the overall leakage current in ESU 34. Further, the current feedback is used to compensate for non-linearities in the AC RF voltage output estimation from the DC voltage input feedback. Similarly, the DC voltage input feedback is used to improve AC current feedback estimation. The DC voltage feedback value is multiplied by a constant, calculated for each RF mode, and added to the AC current feedback estimation.

When circuit 46 of FIG. 3 is compared to the prior art circuit 10 of FIG. 1, it is evident that the number of components in circuit 46 has been reduced. Circuit 46 has a fewer number of components, does not require RMS converters and transformers which are costly, and its design results in a lowered overall capacitance across isolation barrier 48. The result is a more cost-efficient feedback estimation circuit, with reduced leakage current. Circuit 46 shown in FIG. 3 includes microprocessor 62. Microprocessor 62 may be programmable to execute algorithms stored in memory, where the algorithms estimate the RMS output voltage and provide a control PWM signal 64 at location (4) which controls the power output of the RF generator. Microprocessor 62 receives two input signals, a signal 66 representing the DC input voltage feedback measured by voltage sensor 56 at location (1), and a signal 68 representing the output current measured by current sensor 58 at location (2). Microprocessor 62 may use calibration techniques to calibrate the RMS output voltage using input signals 66 and 68. In one embodiment, using the DC input voltage and the output current as independent explanatory variables, a multiple linear regression analysis can be used to estimate the dependent variable RMS output voltage. Using appropriate control ranges and calibration points, an accurate estimate of the RMS output voltage can be obtained. As discussed above, because the actual output voltage feedback is not being measured, but rather is being estimated, circuit 46 does not require additional transformers and RMS converters as needed by prior art circuits. Once an estimate of the RMS output voltage has been obtained, microprocessor 62 can use the estimate RMS output voltage and the measured output current to output a PWM control signal 64 in order to control the DC input voltage to the RF waveform generator 60 and the power delivered to the patient by ESU 34 to desired levels.

The present disclosure advantageously provides an ESU 34 having an RF generator circuit 46 that eliminates the need to measure voltage output feedback in order to control the power output of the RF generator 36, thus reducing the number of expensive RMS converters and transformers needed to measure output voltage feedback. Instead, circuit 46 provides input signals representing the input voltage and the measured AC current feedback to microprocessor 62, which performs a calibration technique such as a regression analysis to estimate the output voltage feedback. Based on the estimated output voltage feedback and the measured current feedback, microprocessor 62 can estimate the power and adjust PWM signal 64 accordingly in order to control the DC voltage input into the RF waveform generator 60 and control the overall power delivered by ESU 34. The result is an ESU 34 that has an improved and accurate feedback estimation system to regulate RF energy control in order to avoid the delivery of excess RF energy to the patient while including a reduced number of transformers and internal inductance couplings, thus minimizing the likelihood of leakage current.

Figure 4:
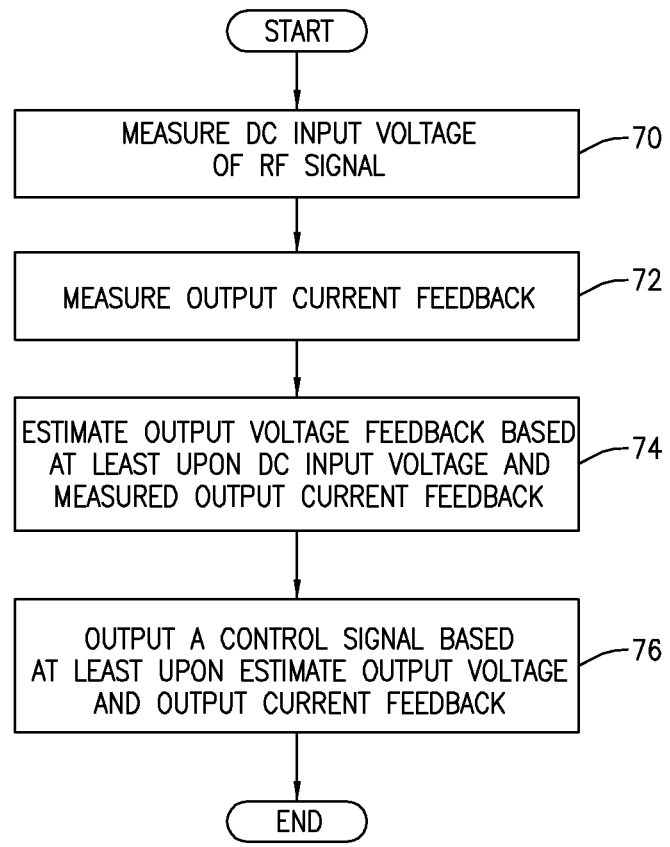
FIG. 4 illustrates a process flow of the embodiment depicted in FIG. 3.

FIG. 4 illustrates a process flow of one embodiment of the present disclosure. The DC input voltage component of the RF signal is measured by voltage sensor 56, at step 70. The output current feedback is measured by current sensor 58, at step 72. The output voltage feedback is estimated, rather than measured, where the estimated output voltage based at least upon the DC input voltage and the measured output current feedback, at step 74. Microprocessor 62 outputs a control PWM signal 64, where the control signal is based at least upon the estimated output voltage and the measured output current feedback, at step 76.

Figure 5:
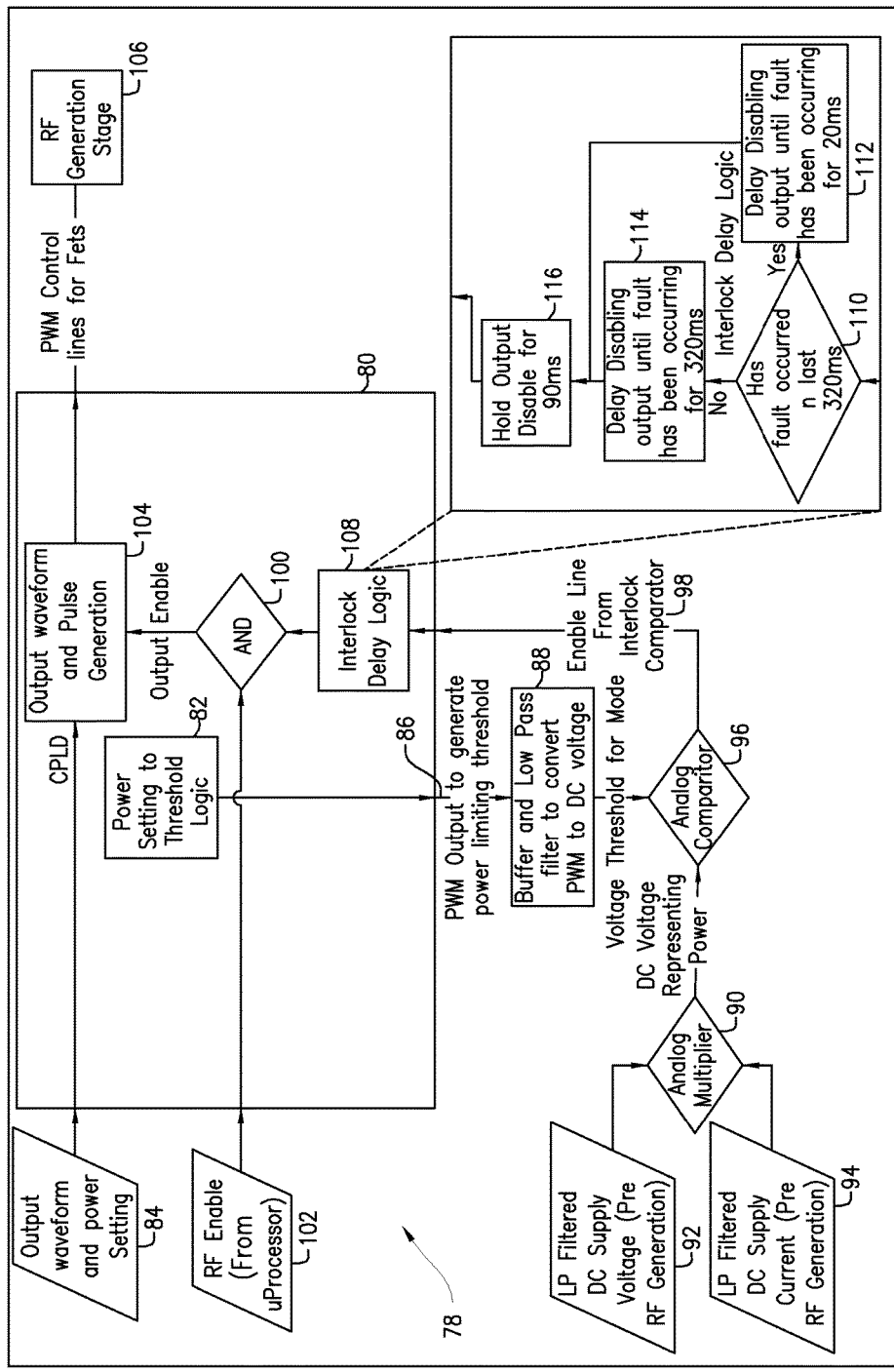
FIG. 5 illustrates a power output limiting circuit according to another embodiment of the present disclosure.

FIG. 5 illustrates another embodiment of the present disclosure. In FIG. 5, ESU 34 is shown to include a hardware-based power output circuit 78. Circuit 78 limits RF energy being delivered to a patient in order to comply with standards such as IEC 60601, which requires that the therapeutic energy delivery system maintain safe operation during normal and fault conditions.

Circuit 78 includes a programmable logic device 80 such as an application specific integrated circuit ("ASIC"), field programmable gate array ("FPGA") or a complex programmable logic device ("CPLD"). The term CPLD will be used throughout the present disclosure, although the present disclosure is not limited to a specific type of programmable logic device. Using threshold logic 82, CPLD 80 receives an output waveform and required power setting 84 where the power setting is based on a specific power limit value. The power limit value input to CPLD 80 could be based on a specific power threshold that ESU 34 must not exceed in order to maintain safe operation, such as, for example, power thresholds identified in IEC 60601. Using the power setting, CPLD 80 outputs a PWM signal 86 that is proportional to the specific power limit value that it corresponds to. The PWM signal 86 represents a power limiting threshold. PWM signal 86 is filtered by a buffer and low pass filter 88 or other similar filtering circuitry, in order to convert PWM signal 86 to a corresponding DC reference voltage.

Circuit 78 also includes an analog multiplier 90. Analog multiplier 90 receives a filtered DC supply voltage 92 and a DC supply current 94 that are input into the RF generator circuit (not shown in FIG. 6). Analog multiplier 90 outputs the product of the DC supply voltage and the DC supply current in the form of a power signal. An analog comparator 96 compares the power signal output from analog multiplier 90 with the voltage threshold output (which represents the power limit) by the buffer and low pass filter 88. If the DC voltage component of the power signal is less than the voltage threshold, an enable signal 98 is input to CPLD 80. Logic conjunction circuitry 100 couples the enable signal 98 with an RF enable signal 102 received from the microprocessor (not shown) to enable a PWM generator 104 to output the waveform and PWM signal where the PWM signal is used to produce the RF energy output at the RF generation stage 106. Thus, in this manner, RF energy delivered to the patient will not exceed a specified limit and safe operation can occur in compliance with safety standards, for example, IEC 60601-2-2 mitigation for single-fault conditions.

If analog comparator 96 compares the power signal output from analog multiplier 90 with the voltage threshold output by the buffer and low pass filter 88 and determines the DC voltage component of the power signal exceeds the voltage threshold, enable signal 98 can be delayed in order to filter onset and removal of disruption of RF signal generation. Interlock delay logic 108 delays the removal of the enable signal for a predetermined amount of time thus delaying the interruption of the generation of the PWM control signal to RF generation stage 106. Once the over power condition represented by signal 98 exceeds the onset delay, the enable into logic conjunction circuitry 100 is disrupted for a minimum delay period controlled by delay logic 108, preventing RF signal generation. Thus, delay logic 108 can be configured to delay output of the PWM control signal from CPLD 80 for a period of time equal to a fault duration.

Figure 6:
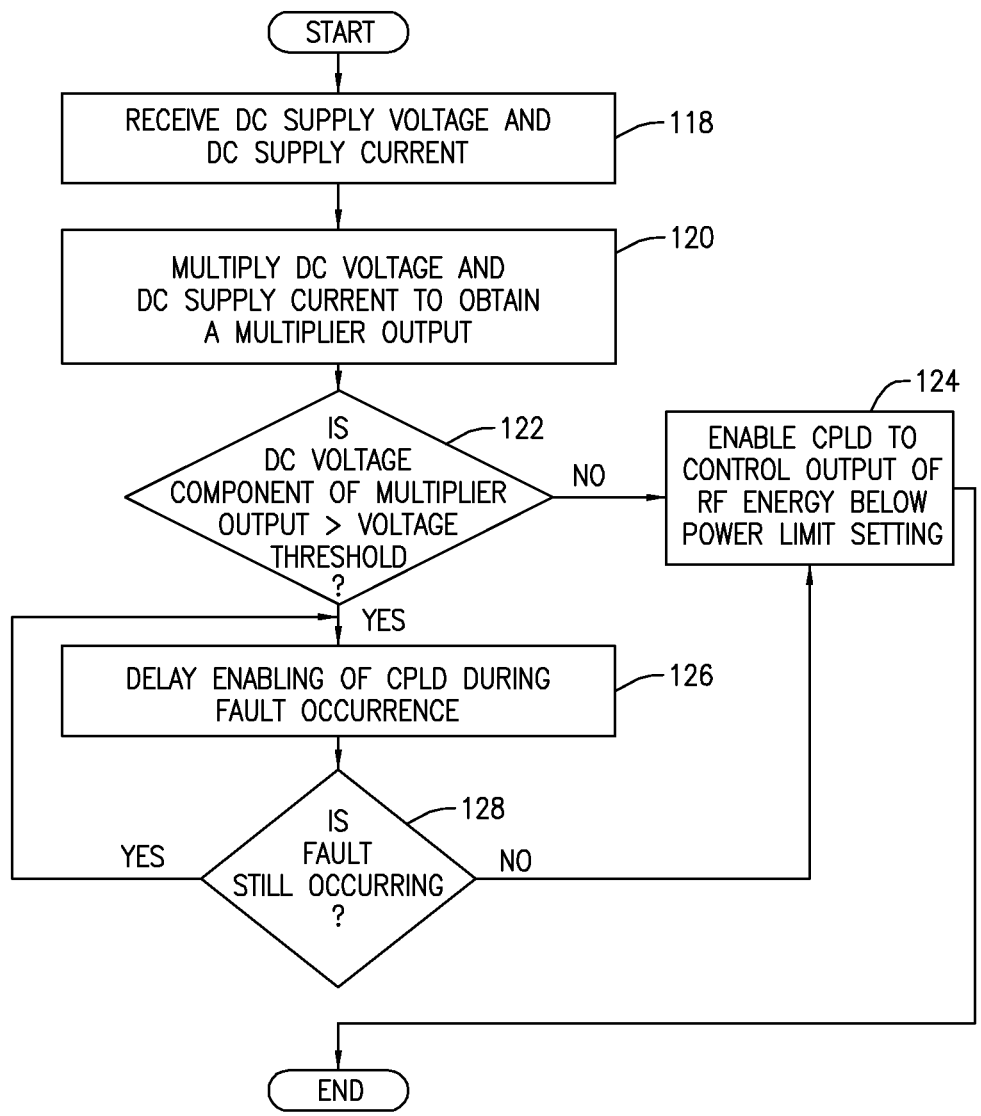
FIG. 6 illustrates a process flow of the embodiment depicted in FIG. 5.

The time durations shown for interlock delay logic 108 in FIG. 6 are merely exemplary, and the delay logic described herein can be adjusted to use any time duration parameters. In an exemplary series of steps performed by interlock delay logic 108, it is first determined if a fault condition exists and if so has the fault occurred within a predetermined amount of time, at step 110. For example, if it is determined that the fault has occurred in the last 320 msec., the disabling output is delayed until the fault has been occurring for a predetermined amount of time, i.e., 20 msec., at step 112. If a fault has not occurred within the past 320 msec., the disabling output is delayed until the fault has been occurring for 320 msec., at step 114. The disabling output signal is then held for a duration of time, i.e., 90 msec., at step 116. Thus, interlock delay logic 108 can allow or inhibit enable signal 98 from comparator 96 depending upon the duration of the fault condition. By delaying or inhibiting enable signal 98, the result of the logic conjunction circuitry 100 is "0", thus delaying the generation of the PWM control signal to RF generation stage 106 during fault conditions.

FIG. 6 illustrates the process flow of circuit 78 according to an embodiment of the present disclosure. DC supply voltage and DC supply current are received, at step 118, and multiplied to form a multiplier output, at step 120. The DC voltage component of the multiplier output is compared to the voltage threshold, at step 122. As described above, the voltage threshold is based on the PWM output by CPLD 80, which is based on the required power setting 84. If the DC component of the multiplier output is not greater than the threshold voltage, an enable signal is sent to CPLD 80 to enable CPLD 80 to control the output of RF energy below the power limit setting, at step 124, to be used at the RF generation stage 106. If the DC voltage component of the multiplier output is greater than the voltage threshold, delay logic 108 delays the disabling and re-enabling of CPLD 80, thus preventing waveform output during, for example, fault conditions, at step 126. Once it is determined that the fault is no longer occurring, at step 128, CPLD 80 may be enabled as described above.

It will be appreciated by persons skilled in the art that the present disclosure is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the present disclosure, which is limited only by the following claims.

What is claimed is:

1. An electrosurgical unit comprising:
    a power source configured to produce direct current;
    a radiofrequency (RF) waveform generator configured to convert the direct current (DC) into an RF signal;
    a voltage sensor configured to measure a DC input voltage to the RF waveform generator;
    a current sensor configured to measure an output alternating current (AC) current feedback; and
    a processor configured to:
        estimate output AC voltage feedback based at least upon the measured DC input voltage and the measured output AC current feedback, the estimated output AC voltage feedback is not based at least in part on measurement of the output AC voltage feedback; and
        output a control signal to control the DC input voltage to the RF waveform generator, the control signal based at least upon the estimated output AC voltage feedback.

2. The electrosurgical unit of claim 1, wherein the RF waveform generator comprises a bridge circuit configured to generate the RF signal from the DC input voltage adjusted by the processor.

3. The electrosurgical unit of claim 2, where the voltage sensor measures the DC input voltage to the bridge circuit.

4. The electrosurgical unit of claim 1, further comprising an isolation barrier in electrical communication with the RF waveform generator.

5. The electrosurgical unit of claim 1, wherein the processor estimates the output AC voltage feedback using a statistical analysis mechanism.

6. The electrosurgical unit of claim 5, wherein the statistical analysis mechanism is a multiple linear regression analysis where analog to digital conversion (ADC) readings for the measured DC input voltage and alternating current root-mean-square (AC RMS) readings for the measured output AC current feedback are used as independent variables.

7. The electrosurgical unit of claim 1, wherein the estimated output AC voltage feedback is not based at least in part on measurement of a DC input current to the RF waveform generator.

8. A method for controlling power of radiofrequency (RF) system, the method comprising;
    measuring a direct current (DC) input voltage to an RF waveform generator;
    measuring an output alternating current (AC) current feedback;
    estimating output AC voltage feedback based at least upon the measured DC input voltage and the measured output AC current feedback, the estimated output AC voltage feedback is not based at least in part on measurement of the output AC voltage feedback; and
    outputting a control signal to control the DC input voltage to the RF waveform generator, the control signal based at least upon the estimated output AC voltage feedback.

9. The method of claim 8, wherein estimating the output AC voltage feedback comprises using a statistical analysis mechanism.

10. The method of claim 9, wherein the statistical analysis mechanism is a multiple linear regression analysis where analog to digital conversion (ADC) readings for the measured DC input voltage and alternating current root-mean-square (AC RMS) readings for the measured output AC current feedback are used as independent variables.

11. The method of claim 10, further comprising using the measured output AC current feedback to compensate for non-linear behavior in the estimated output AC voltage feedback.

12. The method of claim 8, wherein the estimated output AC voltage feedback is not based at least in part on measurement of a DC input current to the RF waveform generator.

* * * * *